(12) United States Patent
Spiegelman et al.

(10) Patent No.: US 8,664,004 B2
(45) Date of Patent: Mar. 4, 2014

(54) METHOD FOR ANALYSIS OF CONTAMINANTS IN A PROCESS FLUID STREAM

(75) Inventors: Jeffrey J. Spiegelman, San Diego, CA (US); Daniel Alvarez, Jr., San Diego, CA (US); Allan Tram, San Diego, CA (US)

(73) Assignee: Entegris, Inc., Billerica, MA (US)

( * ) Notice: Subject to any disclaimer, the term of this patent is extended or adjusted under 35 U.S.C. 154(b) by 1950 days.

(21) Appl. No.: 10/544,309

(22) PCT Filed: Feb. 20, 2004

(86) PCT No.: PCT/US2004/004845
§ 371 (c)(1),
(2), (4) Date: Nov. 29, 2005

(87) PCT Pub. No.: WO2004/077015
PCT Pub. Date: Sep. 10, 2004

(65) Prior Publication Data
US 2006/0211131 A1    Sep. 21, 2006

Related U.S. Application Data

(60) Provisional application No. 60/449,284, filed on Feb. 21, 2003.

(51) Int. Cl.
*G01N 1/40* (2006.01)
(52) U.S. Cl.
USPC ........... 436/178; 436/177; 436/174; 73/31.03

(58) Field of Classification Search
USPC .......................... 436/174, 177, 178
See application file for complete search history.

(56) References Cited

U.S. PATENT DOCUMENTS

| | | | | |
|---|---|---|---|---|
| 4,805,441 A | * | 2/1989 | Sides et al. | 73/23.25 |
| 5,027,642 A | * | 7/1991 | Wen et al. | 73/23.2 |
| 5,138,869 A | * | 8/1992 | Tom | 73/31.03 |
| 5,304,796 A | | 4/1994 | Siefering et al. | |

(Continued)

FOREIGN PATENT DOCUMENTS

| EP | 0 651 247 A1 | 5/1992 |
|---|---|---|
| EP | 1595132 | 1/2007 |

(Continued)

OTHER PUBLICATIONS

Yushchenko et al. A method to calculate density distribution of adsorption centers from temperature-programmed desorption spectra. React. Kinet. Catal. Lett. vol. 40. No. 2. pp. 235-240 (1989).*

(Continued)

*Primary Examiner* — Christopher A Hixson
(74) *Attorney, Agent, or Firm* — Hamilton, Brook, Smith & Reynolds, P.C.

(57) ABSTRACT

The present invention relates to the monitoring of contaminant concentrations in manufacturing processes that employ fluid purification devices. The invention provides a sensitive method for analyzing contaminant concentrations in a process fluid stream using purification material to adsorb contaminants contained therein over an entire process.

38 Claims, 4 Drawing Sheets

(56) References Cited

U.S. PATENT DOCUMENTS

| | | | |
|---|---|---|---|
| 5,447,053 A * | 9/1995 | Ohmi | 73/31.03 |
| 5,511,409 A | 4/1996 | Knaebel | |
| 6,059,859 A | 5/2000 | Alvarez et al. | |
| 6,241,955 B1 * | 6/2001 | Alvarez, Jr. | 423/210 |
| 6,361,696 B1 | 3/2002 | Spiegelman et al. | |
| 6,391,090 B1 * | 5/2002 | Alvarez et al. | 95/116 |
| 6,393,894 B1 | 5/2002 | Bonne et al. | |
| 6,397,660 B1 | 6/2002 | Kikuchi et al. | |
| 6,409,801 B1 * | 6/2002 | Shen et al. | 95/130 |
| 6,418,781 B1 | 7/2002 | Nishina et al. | |
| 6,547,861 B2 * | 4/2003 | Funke et al. | 96/108 |
| 6,550,308 B2 | 4/2003 | Kikuchi et al. | |
| 2001/0025524 A1 * | 10/2001 | Ishiwari et al. | 73/104 |
| 2002/0139167 A1 * | 10/2002 | Schram et al. | 73/1.05 |
| 2003/0162305 A1 | 8/2003 | Alvarez, Jr. et al. | |

FOREIGN PATENT DOCUMENTS

| | | |
|---|---|---|
| JP | 2000-258395 | 9/2000 |
| JP | 2000-304734 | 11/2000 |
| JP | 2001-235405 | 8/2001 |
| SG | 114079 | 9/2007 |
| WO | WO 96/01423 | 1/1996 |
| WO | WO 2005/021134 A1 | 3/2005 |

OTHER PUBLICATIONS

Gilar, Martin et al. "Advances in sample preparation in electromitigation, chromatographic, and mass spectrometric separation methods." *Journal of Chromatography A* (2001) 909 111-135.*

Nakamoto, T. et al. "Odor-sensing system using preconcentrator with variable temperature." *Sensors and Actuators B* (2000) 69 58-62.*

Castello, G., et al., "Automated Gas Chromatographic Analysis of Volatile Organic Compounds in Air", *Journal of Chromatography A, Elsevier Science, NL*, 710(1):61-70, (Aug. 25, 1995).

Jiang, X, et al., "Photolithography Advances Push Purge-Gas Purification", *Solid State Technology*, 45(11):53-54, 56 (Nov. 2002).

Office Action from European Patent Office for EP 04 713 293.1, dated Jan. 31, 2006.

Office Action from European Patent Office for EP 04 713 293.1, dated Sep. 5, 2006.

Office Action from the Patent Office of the Peoples' Republic of China, Application No. 200480004583.X, dated Oct. 9, 2008.

Notification Concerning Transmittal of International Preliminary Report on Patentability, and International Preliminary Report on Patentability, International Application No. PCT/US2004/004845, mail date Apr. 27, 2005.

Written Opinion of the International Searching Authority, International Application No. PCT/US2004/004845 dated Oct. 15, 2004.

International Search Report for International Application No. PCT/US2004/004845 dated Oct. 15, 2004.

* cited by examiner

METHOD FOR ANALYSIS OF CONTAMINANTS IN A PROCESS FLUID STREAM

RELATED APPLICATION

This application claims the benefit of U.S. Provisional Application No. 60/449,284, filed on Feb. 21, 2003. The entire teachings of the above application are incorporated herein by reference.

BACKGROUND OF THE INVENTION

There is an ever increasing need for high purity gases and liquids for use in various chemical, medical and pharmaceutical, and manufacturing processes, specifically in microelectronics, e.g., lithography, epitaxy, and thin film processing. One of the challenges facing today's high purity gas and liquid users is measuring contaminants in their process gas. Contaminants present in small amounts, such as parts-per-trillion (ppt) concentrations, can adversely affect the processes, especially over long periods of chronic exposure. Contaminants may occur in impulse or random events which equipment monitoring response time or random nature prevents measurement and containment. By providing purification on line, impulse events may be smoothed and low to undetectable contaminant levels are concentrated in a purifier.

At the ppt and sub-ppt levels of contamination, continuous process monitoring is not feasible with current analytical methods and technologies. Direct injection methods may be imprecise, inaccurate, or cost prohibitive. An example of direct injection method capable of continuous contaminant monitoring is found in U.S. Pat. No. 6,547,861, which describes an APIMS detection method capable of reaching 25 ppt. See, U.S. Pat. Nos. 6,550,308, 6,397,660, 6,418,781 and 5,304,796. However, this system is large, expensive, and requires a skilled analytical chemist or technician to operate. Concentration methods are often employed to monitor contaminants over longer time periods. This method involves placing a concentration device, such as a thermal desorption tube (TDT), into contact with the process fluid. After a certain time period the TDT is removed from the process and sent to an analytical lab for testing. While the TDT method provides low cost analysis of chronic contamination in a process, it suffers from many drawbacks. TDTs are normally specific to a certain class of contaminants, usually hydrocarbons, and often suffer from low contaminant capacities, reducing sampling times and requiring frequent replacement. TDTs do not generally meet the efficiency and capacity requirements of purifiers. TDTs are often incompatible with ultra-high purity (UHP) fluid delivery systems. TDTs are not required elements of fluid delivery systems and, thus, increase the cost and complexity of any fluid delivery system. When installed parallel to the process fluid delivery line, TDTs bleed gas from the process, thus increasing gas use and requiring adequate venting. TDTs are easily cross-contaminated during installation and removal from process fluid lines. The trapping efficiencies of many TDTs are not very high, resulting in lower detection limits of 100 ppt.

There are many possible sources of contamination during industrial processes. Source gases and liquids may contain contaminants. System leaks can generate environmental contaminants. Off-gassing and permeability of tool materials, mainly plastics but also ceramics and stainless steel can be a source of system contamination. Contaminants may arise from the by-products of reactions in the delivery path or UV light induced reactions, e.g., in photolithography. Such potential contaminant sources and their effects on the manufacturing process provide impetus for using point-of-use (POU) purifiers.

Examples of POU purifiers include inorganic adsorbents, including zeolites, silica, alumina and transition metal-based adsorbents; palladium cells; organic polymers, which can be imbedded with adsorbent materials; and others known to those skilled in the art. Exemplary POU purifiers are those taught in U.S. Pat. Nos. 6,391,090; 6,361,696; 6,241,955; and 6,059,859. The POU purifier selected depends on the source of the gas or liquid to be passed through the purifier and the sources of contaminants typically present in the process. Specific contamination issues may vary broadly between gases and liquids, as well as between different classes of gases or liquids. For example, light hydrocarbons (LHC) generally come from impure source gases. Nitrogenous contamination, moisture and organic solvent vapors are generally present in cleanrooms, but may be condensed on surfaces or dissolved in source liquids. Heavy hydrocarbons and refractory compounds (e.g., siloxanes) generally come from plastics, lubricants, and seals used in tools. Oxygen ($O_2$) and carbon dioxide ($CO_2$) typically come from the environment, i.e. leaks in the fluid delivery system. As different contaminants tend to arise from different points in a process, examining contaminants adsorbed by purifiers indicates sources of contamination in a process. The information generated by such an analysis can be used to improve process control. Identification of contamination sources allows for the isolation of the step to determine the effects on the process.

While many purifiers remove contaminants, in most cases the contaminant molecules are destroyed or otherwise modified as they are removed. Therein the contaminant molecules cannot be released from the purifier material or are not released in a discernible form or reproducible concentration. If all hydrocarbon contaminants are converted into carbon dioxide and water or if all sulfur-containing contaminants are released as $SO_2$ or $H_2S$, the true nature of the contaminant as it was adsorbed by the purifier material is indiscernible. For example, non-evaporable getters are thought to adsorb nitrogen to form metal nitrides, oxygen to form metal oxides, hydrogen to form metal hydrides, and hydrocarbons to form metal carbides, each of which can migrate from the surface into the bulk of the getter alloy. In this case the contaminant species cannot be desorbed from the purifier in a chemical state identical to that found in the gas or liquid stream. Furthermore, probably as a result of the solid state diffusion process that occurs in these and many other purifier materials, desorption of the contaminants from the purifier material, even as a chemical relative of the original contaminant species, requires high temperatures, is inaccurate, and involves hazardous conditions.

SUMMARY OF THE INVENTION

The present invention relates to the monitoring of contaminants occurring in manufacturing processes that employ fluid purification devices. More specifically, the present invention provides a sensitive method for analyzing the contaminant concentrations in manufacturing processes that employ gas or liquid purifier materials.

In its broadest embodiment the present invention is a method for obtaining information about the contaminants present in a process gas or liquid. In this embodiment, the method comprises passing the process fluid stream (e.g., the entire volume of the fluid stream) through a purifier material to thereby adsorb contaminants onto the purifier in a manner such that the contaminants retain their integrity and/or do not distort the concentration level of the contaminants; isolating the purifier material from the process fluid stream; desorbing the contaminants from the purifier material; and identifying the contaminants desorbed from the purifier material and determining the concentration thereof using analytical means, wherein the concentration is correlated to the contaminant concentration in the entire volume of the process fluid stream The invention provides a method for the analysis of gas or liquid purifiers used in a manufacturing process to determine contaminants removed from the gas or liquid stream by the purifier. After contact with the gas or liquid stream for a period of time, the purifier is connected to an analytical instrument, e.g., gas chromatography/flame ionization detector (GC/FID) or gas chromatography/mass spectrometry (GC/MS), and the purifier is subjected to conditions to desorb contaminants, e.g., heating, vacuum or addition of alternative gas, to release products bound to the purifier material. Desorption may be effected in a stepwise fashion to release contaminants separately. The desorption stream is analyzed to determine the contaminants present and their concentrations. Using data from a particular purifier and process conditions, information about the process may be extrapolated. The information can be used to improve process control.

The chemical or physical action of an alternative gas can be used to remove the contaminants from the purifier material. In one embodiment, the alternative gas is chemically inert to the contaminant and/or the purification material. In another embodiment, the alternative gas is chemically oxidizing to the contaminant compounds and/or the purification material. In yet another embodiment, the alternative gas is chemically reducing to the contaminant compounds and/or the purification material. In a particularly preferred embodiment, the alternative gas is hydrogen.

The present invention is a method and apparatus for the identification and quantification of contaminants removed from a process gas or liquid by the normal operation of a purifier, wherein the concentration of said contaminant is below the detection limit of analytical equipment commonly used in the manufacturing process or known to those skilled in the art. Detection limits vary by contaminant and analytical equipment varies by manufacturing process, but in this preferred embodiment the extrapolation of contaminant concentrations in the range of about 0.01-1,000 ppt, preferably 0.1-500 ppt, is possible.

In the method of the present invention, the data obtained after analyzing the desorption gas stream quantitatively reflects the contaminant concentration in the process gas or liquid. In order to obtain actual contaminant concentrations in the process gas or liquid, certain process specific information must be known. This information includes the flow rate of process gas or liquid, the total time of purifier use, and the duty cycle of the purifier. This information is commonly known by the operators of a particular manufacturing process and would, thus, readily be obtainable by those skilled in the art.

The method of the present invention requires that contaminants be desorbed from the purifier non-destructively or that they be desorbed from the purifier in a discernible form (e.g., non-destructive). For example, oxygen may be chemisorbed by a purifier material to form an oxide layer and released from the purifier material as water after reduction of the oxide layer, in which case the oxygen concentration is discernible by monitoring the water concentration in the desorption stream. Furthermore, the total oxygen contaminant concentration and total water contaminant concentration may be analyzed separately by, for example, first desorbing the water under non-reducing conditions followed by reductive treatment to release chemisorbed oxygen.

The invention is an apparatus for the analysis of contaminants desorbed from a purifier. Such an apparatus comprises a connector with a valve or other controller to attach the purifier to the device while limiting exchange between the purifier and the apparatus; a heater and thermostat for regulating the temperature of the purifier material; a gas source and a connector with a controller to attach the gas source to the apparatus while limiting exchange between the gas source and the apparatus; and an analytical instrument to detect the desorbed contaminants. The apparatus preferably contains a quantitative analytical instrument to determine the quantity of the contaminants released. Further, the apparatus may contain mass flow controllers and valves, desorption tubes and/or cold traps for collecting contaminants and a computer or other logical tool that can be used for data analysis.

BRIEF DESCRIPTION OF THE DRAWINGS

The present invention will be better understood when consideration is given to the following detailed description thereof. Such description makes reference to the annexed drawings.

DETAILED DESCRIPTION OF THE PREFERRED EMBODIMENTS

Figure 1:
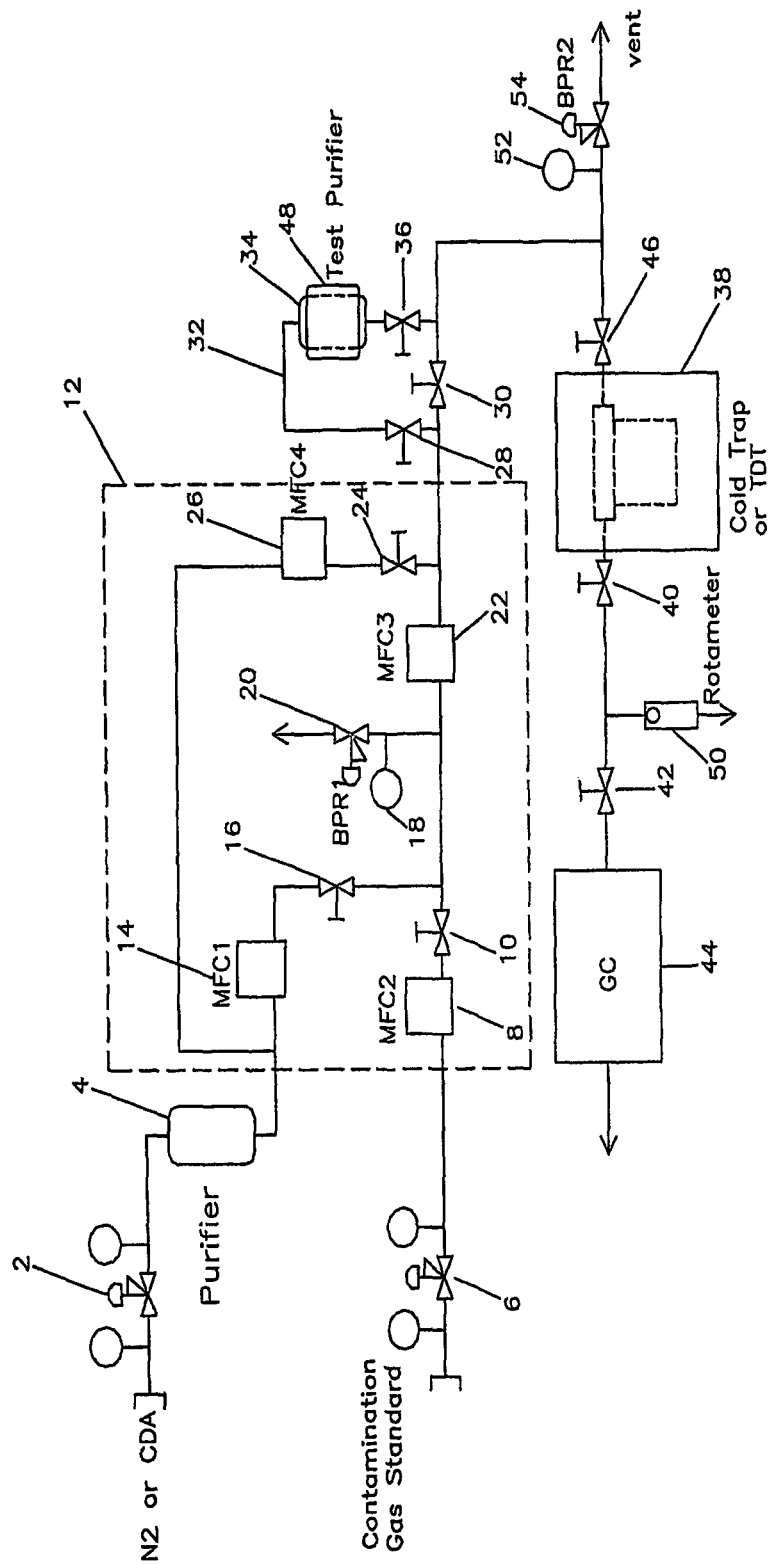
FIG. 1 is a schematic diagram of the apparatus of the present invention, representing a preferred embodiment thereof.

As the demand for higher purity gases has increased, the demand for methods of monitoring gas purification and optimization of methods to reduce contamination have increased. Increasingly sensitive methods are required for the analysis of parts-per-trillion (ppt) and sub-ppt contaminant concentrations, making detection and analysis equipment more complex and expensive. The invention is a method for the sub-0.1 ppm analysis of contaminant concentrations in high purity gases or liquids. The method comprises a purifier that removes the contaminants from a process fluid stream while on line and detection of the contaminants desorbed from the purifier while off line.

An advantage of the invention is that the method can be used to monitor a process fluid streams that contains levels of contaminants that are normally undetectable. The invention allows one to ascertain the concentration of contaminants in a process fluid stream using integrative sampling of the contaminants (i.e., all of the fluid stream passes through the purifier material) so that over time the concentration of adsorbed contaminants in the purifier reaches detectable levels; in contrast to periodic sampling where the contaminant levels are otherwise undetectable. The integrative sampling period can be over the useful life of the purifier material or over the entire life time of the process. This provides a significant advantage over the traditional use of thermal desorption tubes, where only a portion of the process fluid stream is directed through the TDT rather than the entire process fluid stream.

The invention further provides end user access to high sensitivity analysis of contaminants adsorbed by the purifier without having to purchase expensive analysis equipment. The invention may further include analysis of the manufacturing process based on the contaminants desorbed from the purifier allowing optimization of the manufacturing process.

In the method of the present invention, a purifier is installed in a fluid delivery line servicing a manufacturing process. Since purifiers are commonly installed in fluid delivery lines, especially point-of-use purifiers in lines servicing microelectronics process tools, no additional equipment or functional input is required by the end-user to practice the present invention. At a desired point in time, which may be the specified lifetime of the purifier or a specific point in a process as after a major system upset, the purifier is disconnected from the manufacturing process. This may be accomplished by physical deinstallation of the purifier from the fluid delivery line or by closure of the fluid's flow through the purifier material, as in the case of assemblies of valves, mass flow controllers, and other mechanical devices. At this point the required input by the end user has been fulfilled. A desorption gas is then made to flow through the purifier and the effluents, which contain the desorbed contaminants, are monitored by a suitable analytical device. Analysis and quantification of the contaminants over the process period can be made prior to regenerating the purifier material.

While the method of the present invention is not restricted by any specific mechanisms of adsorption and/or desorption, the invention requires the use of specific purifier materials that remove contaminants in a discernible manner. Preferably, contaminants are removed by the purifier non-destructively, but certain other adsorption mechanisms particular to specific purifier materials would also be considered discernible according to the method of the present invention. Purifier materials that are especially suited to the method of the present invention are Gate Keeper™ point-of-use purifiers available from Mykrolis Corporation, Billerica, Mass. The exact adsorption/desorption mechanisms of various contaminants in combination with various types of these purifiers are unknown and speculative, but the requirement of an analytical relationship between process contaminant concentration and contaminants detected by the method of the present invention is met by these purifier materials.

In one embodiment of the invention, an end user of a purifier at regular intervals or upon development of a problem, disconnects the purifier from the apparatus to which it is attached and ships it to the manufacturer or other qualified analyst to determine the contaminants in the process gas or liquid. Alternatively, the purifier may be effectively detached from the apparatus to which it is attached by means of a bypass line. Regardless of the location of the purifier and the analysis equipment, the process for analyzing contaminant concentrations is the same.

The purifier is attached to an analytical instrument, e.g., GC/FID or GC/MS, and the purifier is subjected to conditions to desorb the contaminants including, but not limited to, heating, vacuum, exposure to alternative gases or combinations thereof. The heating may be ramped or stepped to separate contaminants being desorbed separately by strength of the interaction with the adsorbent. Addition of alternative gases can be used to physically and/or chemically release products bound to the media (e.g., injection of hydrogen to release oxygen adsorbed to the media as water). Methods of desorption are well known to those skilled in the art. For thermal desorption, the temperature can be increased linearly or increased in stages to a number of isothermal points.

The contaminant containing stream is analyzed to determine the contaminants present and their concentrations. Contaminants removed from the fluid stream include, but are not limited to, organic compounds (e.g., $C_1$-$C_{20}$ hydrocarbons), carbon dioxide, carbon monoxide, nitrogen-containing compounds (e.g., NO, $NO_2$, $N_2O$, $NH_3$, organic amines, or $NX_3$; wherein X is a halogen atom), sulfur-containing compounds (e.g., $SO_2$, $SO_3$, $H_2S$, organic thiols or thioethers), hydride compounds (e.g., $BH_3$, $AlH_3$, $SiH_4$, $GeH_4$, $NH_3$, $PH_3$, or $AsH_3$), hydrogen, halide compounds (e.g., HF, HCl, HBr, fluorocarbons, chlorocarbons, $SiF_4$, $SiC_4$, $NF_3$, $SF_6$, or organic halides), halogens (e.g., fluorine, chlorine, bromine, iodine), metals (e.g., Li, Na, K, Mg, Ca, Ba, Ti, Zr, Cr, Mo, Mn, Fe, Ni, Cu, Zn or Hg), oxygen, water, refractory compounds (e.g., siloxanes, boron or phosphorus compounds), and combinations thereof. A refractory compound is a compound that has the ability to effect the refraction or diffraction of light.

Contaminants may be identified by methods including, but not limited to, GC retention time, MS fragmentation pattern, and infrared (IR) spectroscopy. For analytical purposes, the contaminants may be further concentrated in the effluent stream using a desorption tube, cold trap, or other method well known to those skilled in the art. Concentration improves the detection limits of the method and provides a method for separating dissimilar contaminants.

Using the data obtained during the analysis of a particular purifier and the process conditions under which it was used, information about the process may be extrapolated. For example, mathematical algorithms may be used to relate the desorption time and temperature of a particular contaminant as a function of its known adsorption properties, thereby extrapolating information about the manner of its adsorption, e.g., time or purifier coverage. This information can be used to improve process control.

Contaminants and their concentrations can be plotted as a function of their desorption temperature and time. This provides information about the process of contamination. The first contaminants desorbed are either the last adsorbed or those least tightly bound by the adsorbent. This information can be useful for process control as it may be related to a specific time in the process, e.g., changing of the source gas or liquid; a tool malfunction or service, e.g., temporal material replacement or service; a process step, e.g., substrate change in a molecular beam epitaxy (MBE) or photolithography tool; or a conflicting process step in the facility.

The data obtained can be used to identify the source of the contaminant, be it input gas quality, system integrity, material out-gassing, or process-product breakdown. This information can be used to optimize the manufacturing process. Thus, the present invention is particularly suited to process analysis after a system upset has occurred, e.g., such noticeable defects in semiconductor wafers as film hazing or unwanted doping.

The apparatus for the analysis of contaminants desorbed from a purifier may comprise any of a number of analyzers depending on the detection levels required and the suspected contaminants based on the purifier to be analyzed and the process in which it is used. Such an apparatus comprises a connector with a valve or other controller to attach the purifier to the device while limiting exchange between the purifier and the apparatus; a heater and thermostat for regulating the temperature of the purifier material; a gas source and a connector with a controller to attach the gas source to the apparatus while limiting exchange between the gas source and the apparatus; and an analytical instrument to detect the desorbed contaminants.

The apparatus preferably contains a quantitative analytical instrument to determine the quantity of the contaminants released. An example of a preferred instrument is a GC/APIMS (atmospheric pressure ionization mass spectrometer) which can separate contaminants according to their boiling points, identify them according to their masses and fragmentation patterns and quantify them by their peak intensities. Currently available GC/APIMS instruments are capable of reaching detection limits of 20 ppt. Less complex analytical tools may also be used to determine total organic content (TOC), total sulfur content (TSC), moisture detectors, and infrared spectrometers. The selection of the detection instrument or instruments is a matter of choice. Such selections are routine for those skilled in the art.

The apparatus may contain mass flow controllers and valves, desorption tubes and/or cold traps for collecting contaminants, and a computer or other logical tool that can be used for data analysis. Software including algorithms for extrapolating process information from the desorption data may be used to analyze the results of the desorption.

In the preferred embodiment shown in FIG. 1, a number of these components are used in the analysis of a purifier. The desorption gas, air, enters the apparatus through pressure regulator 2 and is purified to <1 ppt hydrocarbon contaminants by purifier 4. While this purification step is optional, it is desirable to use a desorption gas of the highest possible purity, because background contamination can interfere with the analysis and limit detection. A known gas standard enters the apparatus through pressure regulator 6. The two gas streams are combined in double dilution manifold 12, comprising MFC2 8, MFC1 14, valve 16, pressure gauge 18, back pressure regulator 20, MFC3 22, valve 24, and MFC4 26. The double dilution manifold is optional, but often is required by limitations in available gas standards and mass flow controller operating parameters. The gas is then sent through valve 30, while bypass loop 32 containing test purifier 34 is isolated by closing valves 28 and 36. The gas enters collection device 38 through valve 46, which is preferably a cold trap but may also be a TDT or similar device, and is vented through rotameter 50. Pressure gauge 52 and back pressure regulator 54 allow for venting of excess gas not going through the cold trap during sample collection. After a certain collection period, gas is released from collection device 38 and flows through valves 40 and 42 to quantitative analytical device 44, which is preferably a gas chromatograph fitted with a suitable detector, e.g., FID for hydrocarbons, PFPD for inorganics, or MS for atmospheric or any contaminants.

After calibration of the analytical device, which is not a necessary step of the method but is preferable under ideal test conditions, valves 28 and 36 are opened, valve 30 is closed, and test purifier 34 is exposed to the desorption gas. As stated desorption may be accomplished in a number of ways. This preferred embodiment favors isothermal desorption, wherein 34 is heated by heating element 48 to a desired temperature at which all effluents are collected. Another embodiment using the apparatus of FIG. 1 employs ramped thermal desorption, wherein the temperature of 34 is increased by 48, e.g., linearly, exponentially, or step-wise, over time and different effluents fractions are collected at different times in the desorption process. Another embodiment that requires modification of the apparatus of FIG. 1 involves the use of an alternative gas to assist in the desorption of contaminants. One slight modification comprised by this embodiment is the substitution of hydrogen for air as the desorption gas. The effluent of 34 flows through 36 and 46 and enters 38, which is preferably a cold trap but may also be a TDT or similar device. After a certain collection period, gas is released from 38 and flows through 40 and 42 to 44, which is preferably a gas chromatograph fitted with a suitable detector, e.g., FID for hydrocarbons, PFPD for inorganics, or MS for atmospheric or any contaminants.

Figure 2:
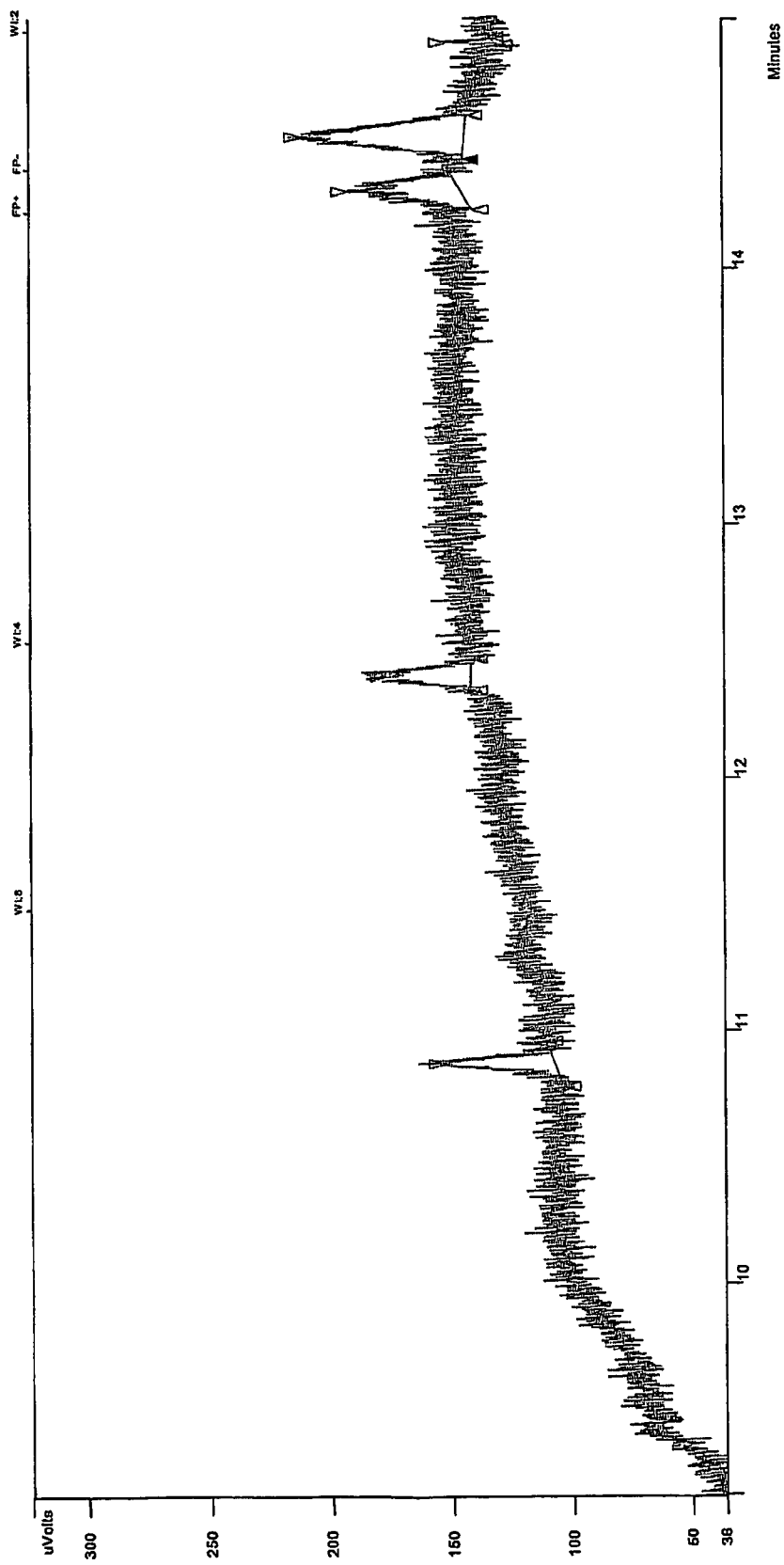
FIG. 2 is a gas chromatograph of a six-component hydrocarbon mixture in air detected by flame ionization detection. The analytes were sampled with a liquid nitrogen cooled cold trap.
Figure 3:
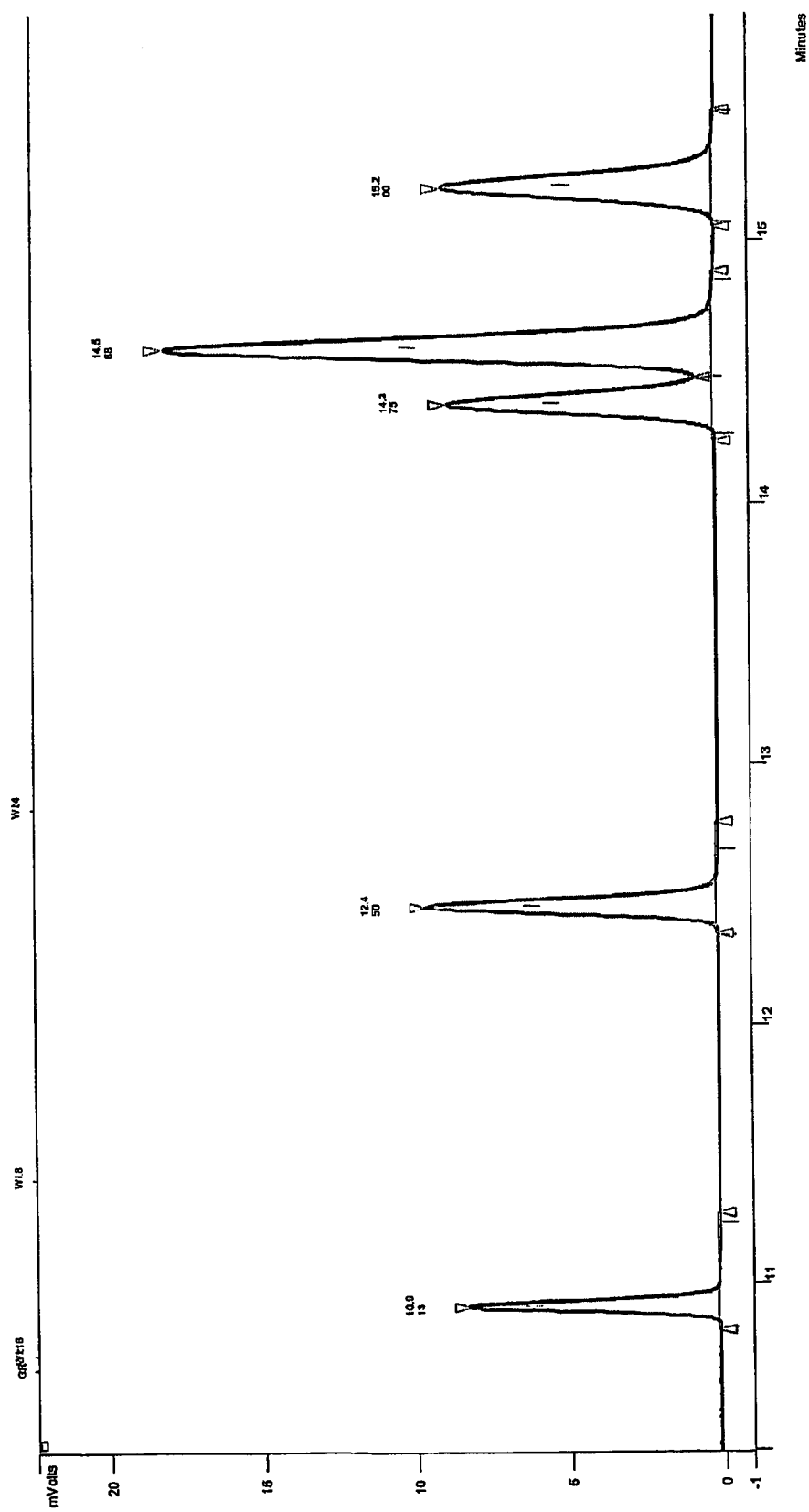
FIG. 3 is a gas chromatograph of a six-component hydrocarbon mixture in air thermally desorbed from a point-of-use purifier and detected by flame ionization detection.
Figure 4:
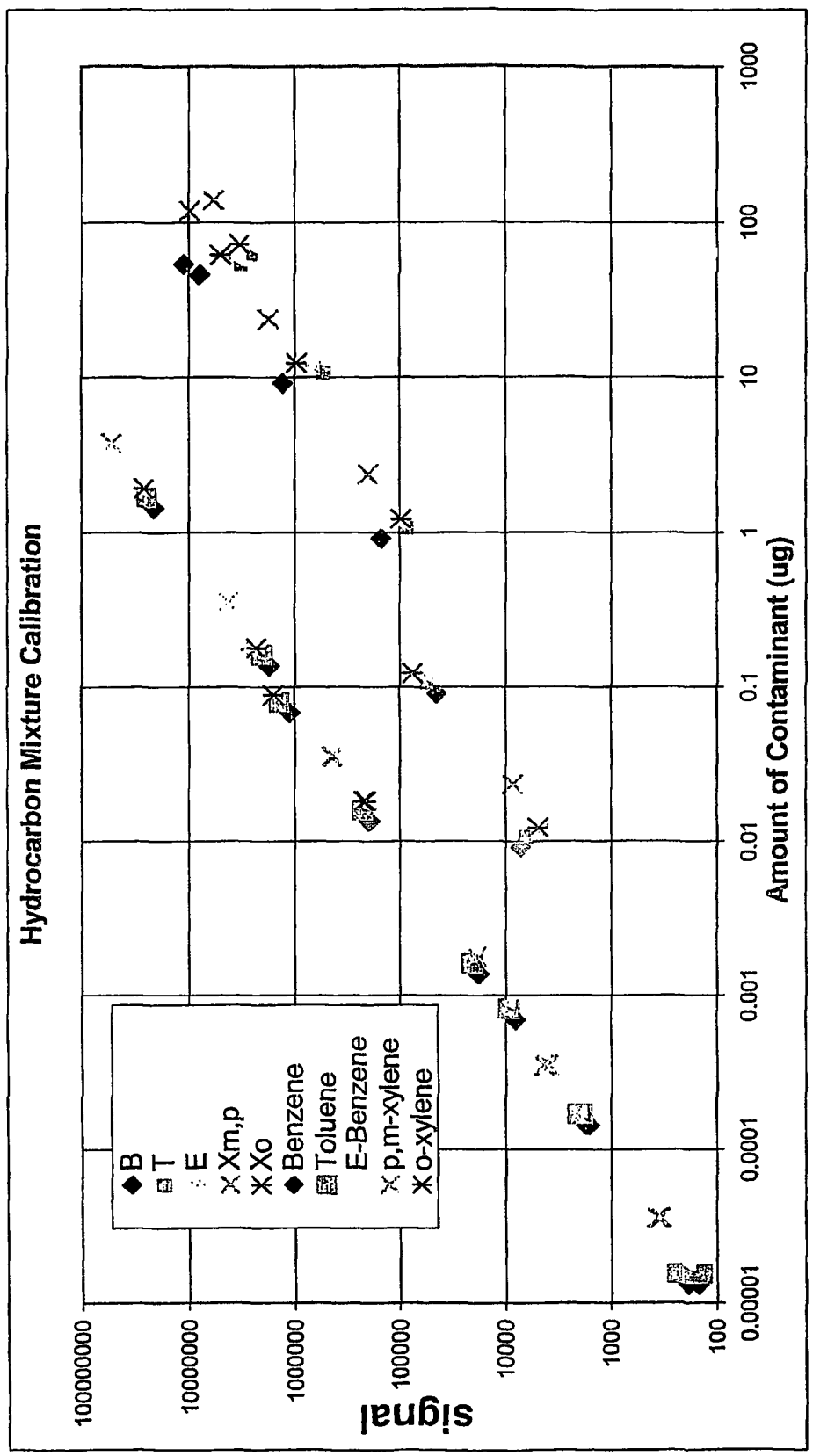
FIG. 4 is a plot of FID response, i.e., detected concentration, versus inlet concentration, calculated from the dilution levels, for varying six-component hydrocarbon mixture concentrations in air. The plot compares the calibration standard thermally desorbed from a test purifier to the same standard when the purifier is bypassed.

FIGS. 2-4 show data obtained using the apparatus of FIG. 1. FIG. 2 is a gas chromatograph of a 10 ppm six-component (benzene, toluene, ethyl benzene, ortho-, meta-, and para-xylene) diluted to 1 ppt and analyzed by the cold trap/° C./FID method. FIG. 3 plots 1 ppb six-component hydrocarbon gas standard desorbed from the test purifier after a 25 minute purification cycle, during which all hydrocarbons were removed to <1 ppt outlet purity, and a 5 minute desorption cycle with air at 300° C. Trace 60 is the 100 ppt hydrocarbon mixture directly sampled by the cold trap/GC/FID method when the test purifier is bypassed. Trace 62 is the same mixture desorbed from the test purifier and analyzed by the cold trap/GC/FID method. The test purifier non-destructively desorbs all of the contaminants originally removed from the test process gas stream. If longer desorption time or higher temperature were used, quantitative desorption could be effected. FIG. 4 is a plot of total inlet exposure of the test purifier to the same six-component hydrocarbon mixture and the total desorbed contaminants after a 5 minute exposure to desorbing gas at 300° C. It can be seen from the combination of FIGS. 2-4 that hydrocarbon analysis according to the method of the present invention is easily accomplished with very low detection limits and, by extrapolation, extremely low contaminant detection in a process gas or liquid stream, either chronic or impulsive. The differentiation between chronic and impulsive contamination requires knowledge of the particular process and, sometimes, a history of the particular fluid delivery system. However, even without this information the method provides contaminant information that would otherwise be inaccessible using prior art methods.

While this invention has been particularly shown and described with reference to preferred embodiments thereof, it will be understood by those skilled in the art that various changes in form and details can be made therein without departing from the spirit and scope of the invention as defined by the appended claims.

We claim:

1. A method for removing contaminants in a manufacturing process fluid stream and analyzing the contaminant concentrations in the manufacturing process fluid stream, comprising:
   a) passing the entire manufacturing process fluid stream for the duration of an entire process period through a purifier material to remove the contaminants from the entire process fluid stream by nondestructively adsorbing contaminants onto the purifier material, wherein the contaminants removed from the process fluid stream are selected from the group consisting of organic compounds, nitrogen-containing compounds, sulfur-containing compounds, hydride compounds, hydrogen, halide compounds, halogens, metals, refractory compounds, and combinations thereof;
   b) isolating the purifier material from the process fluid stream;
   c) nondestructively desorbing the contaminants from the purifier material; and
   d) identifying the contaminants desorbed from the purifier material and determining the concentration thereof, wherein the concentration is correlated to the contaminant concentration in the entire volume of the process fluid stream for the entire process period, and wherein the determination of the contaminant concentration is based on flow rate of the process fluid stream, total use time of the purifier and duty cycle of the purifier.

2. The method of claim 1, wherein the organic compounds comprise $C_1$-$C_{20}$ hydrocarbons.

3. The method of claim 1, wherein the nitrogen-containing compounds comprise NO, $NO_2$, $N_2O$, $NH_3$, organic amines, or $NX_3$; wherein X is a halogen atom.

4. The method of claim 1, wherein the sulfur-containing compounds comprise $SO_2$, $SO_3$, $H_2S$, organic thiols or thioethers.

5. The method of claim 1, wherein the hydride compounds comprise $BH_3$, $AlH_3$, $SiH_4$, $GeH_4$, $NH_3$, $PH_3$, or $AsH_3$.

6. The method of claim 1, wherein the halide compounds comprise HF, HCl, HBr, fluorocarbons, chlorocarbons, $SiF_4$, $SiCl_4$, $NF_3$, $SF_6$, or organic halides.

7. The method of claim 1, wherein the metals comprise Li, Na, K, Mg, Ca, Ba, Ti, Zr, Cr, Mo, Mn, Fe, Ni, Cu, Zn or Hg.

8. The method of claim 1, wherein the refractory compounds comprise siloxanes, boron or phosphorus compounds.

9. The method of claim 1, wherein desorption of the contaminants comprises thermal desorption, use of an alternative gas, or combinations thereof.

10. The method of claim 9, wherein the thermal desorption is isothermal desorption.

11. The method of claim 9, wherein the temperature of the thermal desorption is linearly increased.

12. The method of claim 9, wherein the temperature of the thermal desorption is increased in stages to a number of isothermal points.

13. The method of claim 9, wherein the alternative gas is chemically inert to the contaminant compounds and/or purification material.

14. The method of claim 9, wherein the alternative gas is hydrogen.

15. The method of claim 9, wherein certain contaminants are first removed from the purification material by thermal desorption and other contaminants are second removed from the purification material by the physical action of an alternative gas.

16. The method of claim 1, wherein detecting the contaminants comprises using a gas chromatography/flame ionization detector, a gas chromatography/mass spectrometer, or gas chromatography/atmospheric pressure ionization mass spectrometer.

17. A method for removing contaminants in a manufacturing process fluid stream and determining the historic contamination concentration in the manufacturing process fluid stream, comprising:
   a) passing the entire manufacturing process fluid stream for the duration of an entire process period through a purifier to remove contaminants from the process fluid stream, the purifier comprising a purifier material capable of non-destructively removing contaminants from the process fluid stream from an original contaminant concentration that is below the detection limit of an on line analytical device to a final contaminant concentration that is detectable by the analytical device;
   b) isolating the purifier material from the process fluid stream;
   c) removing contaminants from the purifier in a non-destructive manner; and
   d) analyzing an effluent gas produced from removing contaminants from the purifier to thereby determine the historic contaminant concentration in the process fluid stream over the duration of the entire process period.

18. The method of claim 17, wherein the original contaminant concentration is about 10 ppb, about 5 ppb, or about 1 ppb.

19. The method of claim 17, wherein the original contaminant concentration is less than about 1 ppb, less than about 0.1 ppb, or less than about 0.01 ppb.

20. The method of claim 17, wherein the contaminants are removed from the purification materials by thermal desorption.

21. The method of claim 20, wherein the thermal desorption is isothermal desorption.

22. The method of claim 20, wherein the temperature of the thermal desorption is linearly increased.

23. The method of claim 20, wherein the temperature of the thermal desorption is increased in stages to a number of isothermal points.

24. The method of claim 17, wherein the removing step further comprises the use of a physical action of an alternative gas.

25. The method of claim 24, wherein the alternative gas is chemically inert to the contaminant compounds and/or purification material.

26. The method of claim 24, wherein the alternative gas is hydrogen.

27. The method of claim 17, wherein certain contaminants are first removed from the purification material by thermal desorption and other contaminants are second removed from the purification material by the physical action of an alternative gas.

28. The method of claim 17, wherein the analysis comprises using a gas chromatography/flame ionization detector, a gas chromatography/mass spectrometer, or gas chromatography/atmospheric pressure ionization mass spectrometer.

29. The method of claim 17, wherein the removing step includes regenerating the purifier material for reuse in another process fluid stream.

30. The method of claim 17, wherein a ratio of the original contaminant concentration of the entire process fluid stream to the final contaminant concentration of the entire process fluid stream is at least 1000:1.

31. The method of claim 17, wherein the manufacturing process fluid stream is a chemical, medical, or pharmaceutical process fluid stream.

32. A method for removing contaminants in a manufacturing process fluid stream and analyzing the contaminant concentrations in the manufacturing process fluid stream, comprising:
   a) passing the entire manufacturing process fluid stream for the duration of an entire process period through a purifier material to remove the contaminants from the entire process fluid stream by nondestructively adsorbing contaminants onto the purifier material, wherein the purifier material comprises an inorganic adsorbent, transition metal adsorbent or palladium cells;
   b) isolating the purifier material from the process fluid stream;
   c) nondestructively desorbing the contaminants from the purifier material to regenerate the purifier material for use in the purification of another process fluid stream; and
   d) identifying the contaminants desorbed from the purifier material and determining the concentration thereof, wherein the concentration is correlated to the contaminant concentration in the entire volume of the process fluid stream for the entire process period, and wherein the determination of the contaminant concentration is based on flow rate of the process fluid stream, total use time of the purifier and duty cycle of the purifier.

33. A method for analyzing contaminant concentrations in a manufacturing process fluid stream, comprising:
   a) providing purifier material having adsorbed non-destructively thereon, contaminants from an entire manufacturing process stream collected over an entire process period;
   b) nondestructively desorbing the contaminants from the purifier material to regenerate the purifier material for use in the purification of another process fluid stream; and
   c) identifying the contaminants desorbed from the purifier material and determining the concentration thereof, wherein the concentration is correlated to the contaminant concentration in the entire volume of the process fluid stream for the entire process period, wherein the contaminants removed from the fluid-process fluid stream are selected from the group consisting of organic compounds, nitrogen-containing compounds, sulfur-containing compounds, hydride compounds, hydrogen, halide compounds, halogens, metals, refractory compounds, and combinations thereof, and wherein the determination of the contaminant concentration is based on flow rate of the process fluid stream, total use time of the purifier and duty cycle of the purifier.

34. A method for analyzing contaminant concentrations in a manufacturing process fluid stream, comprising:
   a) providing purifier material having adsorbed non-destructively thereon, contaminants from an entire manufacturing process fluid stream collected over an entire process period, wherein the purifier material comprises an inorganic adsorbent, transition metal adsorbent or palladium cells;
   b) nondestructively desorbing the contaminants from the purifier material to regenerate the purifier material for use in the purification of another process fluid stream; and
   c) identifying the contaminants desorbed from the purifier material and determining the concentration thereof, wherein the concentration is correlated to the contaminant concentration in the entire volume of the process fluid stream for the entire process period, and wherein the determination of the contaminant concentration is based on flow rate of the process fluid stream, total use time of the purifier and duty cycle of the purifier.

35. The method of claim 1, wherein nondestructively desorbing the contaminants from the purifier material further serves to regenerate the purifier material for use in the purification of another process fluid stream.

36. The method of claim 1, wherein the purifier material comprises an inorganic adsorbent, transition metal adsorbent or palladium cells.

37. The method of claim 36, wherein the inorganic adsorbent comprises zeolites, silica or alumina.

38. The method of claim 17, wherein the purifier material comprises an inorganic adsorbent, transition metal adsorbent or palladium cells.

* * * * *

UNITED STATES PATENT AND TRADEMARK OFFICE
CERTIFICATE OF CORRECTION

PATENT NO. : 8,664,004 B2  
APPLICATION NO. : 10/544309  
DATED : March 4, 2014  
INVENTOR(S) : Jeffrey J. Spiegelman et al.

Page 1 of 1

It is certified that error appears in the above-identified patent and that said Letters Patent is hereby corrected as shown below:

In the Claims

Column 9, Line 17, Claim 5, delete "A1H$_3$" and insert -- AlH$_3$ --.

Column 11, Line 21, Claim 33, delete "fluid-process" and insert -- process --.

Signed and Sealed this  
Seventeenth Day of June, 2014

Michelle K. Lee  
*Deputy Director of the United States Patent and Trademark Office*

UNITED STATES PATENT AND TRADEMARK OFFICE
CERTIFICATE OF CORRECTION

PATENT NO.        : 8,664,004 B2                                         Page 1 of 1
APPLICATION NO. : 10/544309
DATED             : March 4, 2014
INVENTOR(S)       : Spiegelman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2215 days.

Signed and Sealed this
Twenty-ninth Day of September, 2015

Michelle K. Lee
*Director of the United States Patent and Trademark Office*